(12) United States Patent
Karlinsey

(10) Patent No.: US 9,724,277 B2
(45) Date of Patent: Aug. 8, 2017

(54) MICROBEADS FOR DENTAL USE

(71) Applicant: Robert L. Karlinsey, Indianapolis, IN (US)

(72) Inventor: Robert L. Karlinsey, Indianapolis, IN (US)

( * ) Notice: Subject to any disclaimer, the term of this patent is extended or adjusted under 35 U.S.C. 154(b) by 92 days.

(21) Appl. No.: 13/860,007

(22) Filed: Apr. 10, 2013

(65) Prior Publication Data

US 2013/0224690 A1     Aug. 29, 2013

Related U.S. Application Data

(63) Continuation-in-part of application No. 13/438,318, filed on Apr. 3, 2012.

(60) Provisional application No. 61/471,649, filed on Apr. 4, 2011.

(51) Int. Cl.
| | |
|---|---|
| *A61C 5/00* | (2017.01) |
| *A61K 8/02* | (2006.01) |
| *A61C 11/00* | (2006.01) |
| *A61K 6/06* | (2006.01) |
| *A61K 6/00* | (2006.01) |
| *A61K 6/02* | (2006.01) |
| *A61K 8/25* | (2006.01) |
| *A61K 8/29* | (2006.01) |

(52) U.S. Cl.
CPC ............ *A61K 8/0283* (2013.01); *A61C 11/00* (2013.01); *A61K 6/0008* (2013.01); *A61K 6/0235* (2013.01); *A61K 6/0612* (2013.01); *A61K 8/25* (2013.01); *A61K 8/29* (2013.01)

(58) Field of Classification Search
CPC .......................... A61K 6/0017; A61K 2300/00
USPC ...... 424/49, 52, 57, 400–401; 427/2.1, 2.29; 433/215, 217.1, 226, 228.1
See application file for complete search history.

(56) References Cited

U.S. PATENT DOCUMENTS

| | | | | |
|---|---|---|---|---|
| 5,718,885 | A * | 2/1998 | Gingold | A61K 8/19 |
| | | | | 424/435 |
| 5,735,942 | A * | 4/1998 | Litkowski | A61K 8/22 |
| | | | | 106/35 |
| 6,506,055 | B1 * | 1/2003 | Pashley | A61K 6/0023 |
| | | | | 106/35 |
| 7,182,937 | B2 * | 2/2007 | Xu | A61K 8/19 |
| | | | | 424/440 |
| 2002/0037258 | A1 * | 3/2002 | Dodd | A61K 6/033 |
| | | | | 424/49 |
| 2003/0008263 | A1 * | 1/2003 | Cook | C03C 12/00 |
| | | | | 433/215 |

(Continued)

FOREIGN PATENT DOCUMENTS

CH    WO 2010060653 A2 *  6/2010 ............... A46D 1/00

*Primary Examiner* — Matthew Nelson
(74) *Attorney, Agent, or Firm* — C. John Brannon; Brannon Sowers & Cracraft PC

(57) ABSTRACT

A method for decreasing dental hypersensitivity, including sizing a plurality of non-functionalized microbeads to be between 0.01 μm to 3 μm in diameter, suspending the plurality of non-functionalized microbeads in a fluid matrix to define a dental delivery composition, introducing the dental delivery composition into an oral cavity, introducing respective non-functionalized microbeads into a dental tubule, adhering respective functionalized microbeads each other and to the dental tubule to define an aggregate, and occluding the dental tubule with the aggregate.

10 Claims, 5 Drawing Sheets

(56) References Cited

U.S. PATENT DOCUMENTS

| | | | |
|---|---|---|---|
| 2003/0133885 A1* | 7/2003 | Kleinberg | A61K 8/19 424/54 |
| 2005/0281884 A1* | 12/2005 | Adair | A61K 47/48861 424/489 |
| 2007/0178220 A1* | 8/2007 | Karlinsey | A61K 8/24 427/2.1 |
| 2008/0206716 A1 | 8/2008 | Asgary | |
| 2010/0047742 A1* | 2/2010 | Pitcock, Jr. | A61K 8/19 433/215 |
| 2010/0135932 A1* | 6/2010 | Deckner | A61K 8/25 424/52 |
| 2010/0197824 A1* | 8/2010 | Bissinger | A61K 6/0017 523/116 |
| 2010/0203092 A1* | 8/2010 | Ley | A61K 8/24 424/401 |
| 2010/0261144 A1* | 10/2010 | Fujinami | A61K 6/0073 433/228.1 |
| 2011/0206746 A1* | 8/2011 | Hagar | A61K 8/25 424/401 |
| 2011/0262507 A1* | 10/2011 | Spring | A46D 1/00 424/401 |
| 2012/0093935 A1 | 4/2012 | Dembski | |
| 2013/0164359 A1* | 6/2013 | Deng | A61K 8/0241 424/401 |

\* cited by examiner

MICROBEADS FOR DENTAL USE

CROSS-REFERENCE TO RELATED APPLICATIONS

This patent application claims priority to co-pending U.S. patent application Ser. No. 13/438,318, filed on Apr. 3, 2012, which claimed priority to then co-pending U.S. Provisional Patent Application Ser. No. 61/471,649, filed on Apr. 4, 2011.

BACKGROUND

Dental hypersensitivity is a challenging problem since the oral environment is continuously cycled through periods of demineralization (i.e. loss of mineral through acid attack or physical attrition) and demineralization (i.e. seeding minerals such as fluoride, calcium and phosphate that combine with the existing tooth structure to grow new mineral that can strengthen the enamel and/or dentin). When too much mineral is lost and the demineralization processes cannot keep the pace of replacing the lost mineral, tooth sensitivities ultimately develop. This is further complicated due to natural aging of the tooth and tends to be more common when restorative or implant procedures have been performed. Such sensitivity is typically manifested in pain arising from sudden extreme temperatures (such as drinking ice cold or steamy hot beverages) or changes in pressure, including the act of chewing or biting on brittle surfaces or through probing with a dental explorer or pressurized air. The sensitivities develop due to the exposure of nerves positioned within the dentin component of the tooth structure. Over time, the penetration of acids into and/or the thinning of enamel increases the risk of demineralizing the thin mineral layers in dentin that surround and protect the sensitive nerve endings. These nerves are typically positioned in dentin tubules (about 1-3 µm in diameter and at least 5 µm in length). Without adequate acid-resistant support, these nerves become triggered during an extreme event, such as chewing food, eating ice cream or drinking a hot beverage. Based on various surveys and polls, at least 40% of the population exhibits some dental hypersensitivity. Thus, hypersensitivity remains a challenging problem and opportunity.

There are several treatments currently used to treat hypersensitivity. One treatment is the placement of resins or varnishes on the affected area. This is typically performed by the dental professional, which may require frequent dental visits. Other treatments may include treating with higher levels of fluoride, such as 5,000 ppm fluoride toothpaste available through the dentist, or using a multiple agent product, such as toothpastes containing combinations of calcium, silica, fluoride, phosphate, strontium, and the like. The most common over-the-counter approach typically involves toothpastes containing potassium nitrate: although a barrier is not formed, the nitrate responds to and neutralizes the exposed nerve ending. These approaches have all produces significant benefits, however, problems still occur. For instance, some have aversions to high fluoride products while others may not visit the dentist on a regular basis. Additionally, the resin and potassium nitrate approaches are temporary solutions, requiring continuous use in order to enjoy long-term relief from hypersensitivity. Separately, the mineral formations that develop in and on the dentin through use of a multiple agent combination product may, over time, not provide sufficient protection against acid challenges and/or physical attrition. Therefore, in this disclosure, we describe a novel combination of materials for improved relief from dental hypersensitivity that also avoids the weaknesses associated with these existing therapies.

DETAILED DESCRIPTION

Figure 1:
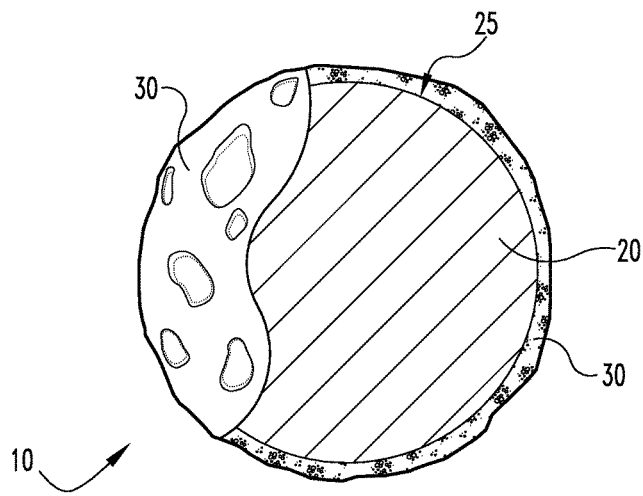
FIG. 1 is a perspective view of a functionalized microbead according to a first embodiment of the present novel technology.
Figure 2A:
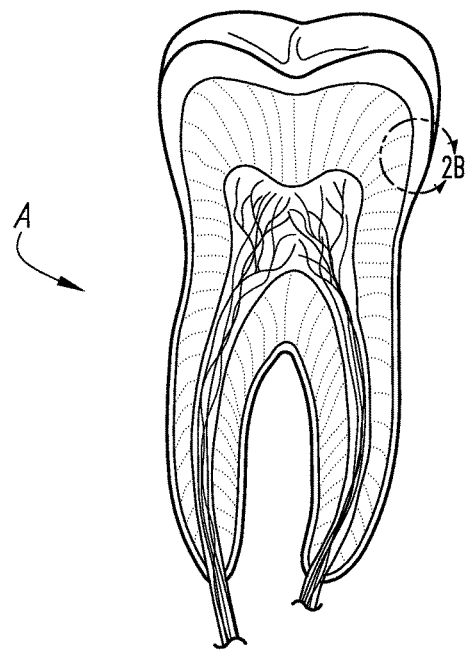
FIG. 2A is a schematic view of a tooth.
Figure 2B:
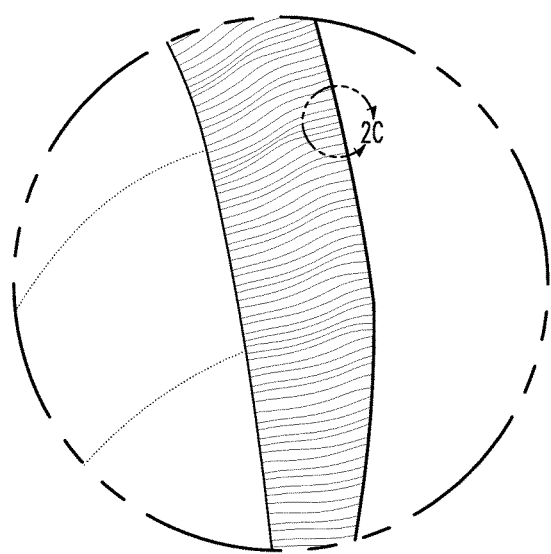
FIG. 2B is an enlarged portion of the tooth of FIG. 2A, illustrating the enamel outer surface.
Figure 2C:
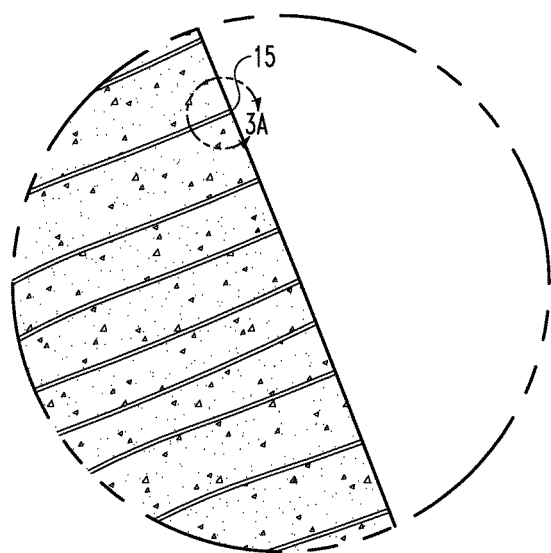
FIG. 2C is an enlarged portion of the enamel outer surface of 2B, illustrating the tubules.
Figure 3A:
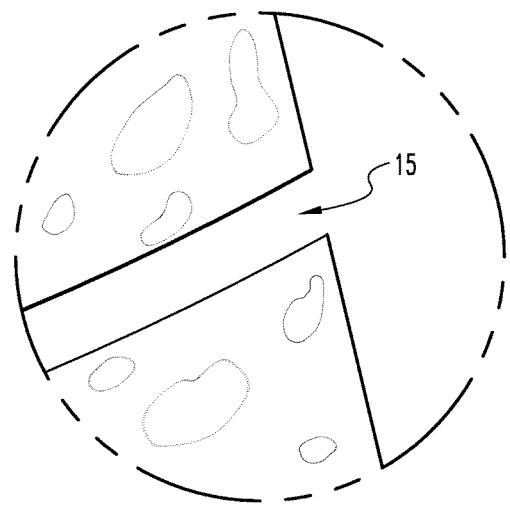
FIG. 3A is an enlarged view of the tubules of FIG. 2C showing a tubule.
Figure 3B:
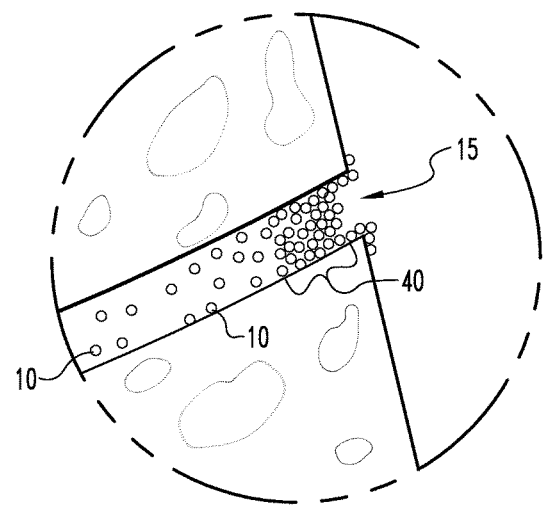
FIG. 3B is a schematic view of the tubule of FIG. 3A occluded with an agglomeration of the microbeads of FIG. 1.

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present technology relates to the general reduction in dental hypersensitivity. One feature of this technology is the incorporation of microbeads 10 into exposed dentin tubules 15. Another feature is the acid-resistant adhesion and retention of the microbeads 10 within the dentin tubules 15 as well as on the weakened dentin surfaces that has resulted from demineralization processes. The microbeads 10 typically include an inorganic microsphere 20 that is coated with a thin organic coating 30. This two-phase system 10 provides a physically strong, acid-resistant layer 30 that adheres to the demineralized dentin surfaces and also occludes dentin tubules 15. This two-phase system 10 can be implemented into dental vehicles including toothpastes, rinses, varnishes, gums, mints, gels, and the like.

Inorganic materials such as silica, titania, alumina, various glass compositions, and the like are commonly found in dental products and are used, for instance, as abrasives, fillers, pigments and/or for providing structural rigidity, and thus may also be used for the inorganic microsphere or core portion 20. Alternately, polymeric microspheres 20 such as polyethylene may also be used for the core portion 20. Microspherical shapes of these materials offer significant benefits relative to other geometries, including yielding large surface areas available for functionalization. Spherical or near-spherical geometry also provides a favorable shape for penetration into demineralized dentin tubules 15, which are porous in nature with diameters between 1 and 4 µm. The spherical shape can also affect light reflection to create a 'whitening-like' effect, both from the reflectivity of the round unfunctionalized silica surfaces, the reflectivity of various coatings, and/or the white color of microspheres composed of titania, alumina or the like.

As shown through in microscopy analysis of demineralized dentin (see figure), the microspheres 10 can readily penetrate into the dentin tubule. Due to differences in the physical and chemical properties between organic (e.g. polymers and the like) and inorganic (e.g., silica and the like) materials, inorganic materials such as silica, titania, and the like can provide structural rigidity and resistance to acid attack, which are attractive and beneficial features when embedded into the relatively softer and acid-susceptible dentin tubules 15.

The present novel technology relates to microbeads 10, typically having dimensions between 0.01 µm to 10 µm, and more typically between 0.9 µm and 3 µm to encourage optimized packing within the dentin tubules. However, other convenient dimensions may be selected. More typically, microbeads 20 are provided with a particle size distribution (PED) defining a variety of diameters within this range for optimal packing and thus the provision of hypersensitivity benefits. Although the microspheres 20 are typically composed of inorganic materials, such as silica, titania, and the like, organic microspheres 20 made from such materials as polyethylene, polypropylene, cross-linked polymers and the like may also be used.

Although the microspheres 20 can penetrate readily into the dentin tubule 15, they are less adept at attaching to the relatively flat dentin surfaces. Therefore, the microsphere surface 25 may include an adhesive coating 20 to encourage greater adhesion of the smooth spherical surface 25 to the smooth dentin surface. Once in the tubule 15, a plurality of microbeads 10 adhere to the tubule walls and each other defining an agglomerate 40 that effectively occludes the tubule 15.

One approach to providing an adhesive coating 30 is to coat or functionalize the inorganic sphere 20 with a hydrophilic or sticky material layer 30. This material 30 can be organic, including a polymer such as polyacrylic acid (e.g. typical molecular weight range between 100,000 and 450,000 g/mol), or another, typically hydrophilic, material. The coating material 30 may be phosphate, such as derived from phosphoric acid. Alternately, the coating material 30 may be hydrophobic, such as derived from silanes or methanes. Typically, the material 30 used to coat the microbeads 20 has some character that encourages mineral seeding and growth so that new mineral can be formed over time within the dentin tubule as well as on the dentin surface. This coating material 30 can attract ions available from both the natural oral environment through saliva components, including calcium, phosphate and the like, and also from the use of dental products containing, for example, fluoride, calcium, phosphate, strontium, potassium, nitrate, tin and the like.

In constructing the functionalized microbeads 10, the typical weight fraction of the organic material 30, such as phosphoric acid, polyacrylic acid and the like, may typically range between 0.01% and 5%, more typically between 0.1% and 1%. The corresponding weight fraction of the organic material 30 should be combined with a suspension or dry powder of inorganic microspheres 20, typically silica or titania. This combination can be achieved using typical chemical approaches including dehydration of a silica suspension followed by addition of the organic agent in the stated amounts coupled with a dehydration step to achieve a dry powder. Alternately, a suspension of the microspheres 20 can be combined with the stated amount of organic agent 30 and left as a suspension.

The two-phase combination 10, comprising microspheres 20 coated with an adhesive layer 30, are able to provide additional benefits relative to use of either agent alone. The adhesive property of the functionalized microsphere 10 can remain on the dentin surface despite challenge from an acid attack, providing structural stability and improved chemical resistance to demineralization from enamel and dentin. The coating 30 serves additional purposes: namely, a sacrificial layer 30 to subsequent acid attacks as well as to promote remineralization through contact with saliva and various dental products with or without fluoride. These factors bear directly on the relief from dentin demineralization and therefore dental hypersensitivity. While either the microbeads 10 alone or the organic coating material 30 alone could offer hypersensitivity relief, the two-phase composite bead 10 can extend hypersensitivity relief. Thus, these composite beads 10 may be implemented into mints, lozenges, gums, rinses, pastes, gels, and the like in form of dry powders or suspensions for delivery to tubules 15 and dentin upon introduction into the oral cavity.

One example of a treatment is the application of a 10% w/v suspension of 1 µm diameter silica microspheres 10 functionalized with 0.5% phosphoric acid coating 30 to demineralized dentin. Application of functionalized microbeads 10 to dentin/tubules may provide greater resistance to acid challenges compared to native (i.e. unfunctionalized) silica microspheres 20.

DETAILED EXAMPLE

One method of functionalizing silica microspheres with phosphate ($PO_4$) was produced with phosphoric acid is as follows:
1) Using a vortex mixer, shake silica suspensions (formulated as discussed above) thoroughly for several minutes.
2) Extract 1 ml of the silica microsphere solution (number of microspheres 10 is approximately $10^9$, $10^{10}$, and $10^{11}$ microspheres 10 for 1.0, 2.5, and 4.0 µm diameter microspheres, respectively) and place in a glass container (i.e. 50 ml Pyrex beaker).
3) Place the beaker with the 1 ml solution into the vacuum oven (warmed to ~100° C.) and slowly pull a vacuum—let it stand for about five minutes or later until the water is removed. Only the silica 20 should remain.
4) To clean the silica 20 and prepare it for functionalization, add several milliliters of ethanol to the resultant powder and then evaporate it—place it in the 100° C. oven for ~10 minutes to remove ethanol.
5) If desired, repeat Step #4 one more time.
6) Separately, make ~0.5% w/w $H_3PO_4$(aq) (i.e. 500-fold dilution of 85% w/w parent solution using distilled water).
7) Add 2 ml of the acidic solution 30 to the silica powder 10 and gently mix—place in oven (e.g. ~100° C. for 15 minutes and slowly pull a vacuum to encourage evaporation.
8) Collect the resultant acid-functionalized silica powder 10, weigh it, and set it aside in a sealed container for later use.

Using $PO_4$ functionalized microspheres 10, bovine dentin was demineralized to expose the ~2-5 µm diameter tubules (50% citric acid solution, ten minutes, room temperature), then treated with a small drop of a 10% suspension (30 mg into 0.3 ml distilled water). Observations were then obtained using scanning electron microscopy.

Amount of Recovered Sample After $PO_4$ Procedure:

| Silica Microsphere Diameter | Mass (mg) |
| --- | --- |
| 1.0 μm | 110.1 |
| 2.5 μm | 114.6 |
| 4.0 μm | 110.6 |

Using $PO_4$ functionalized microspheres, bovine dentin was demineralized to expose the ~2-5 μm diameter tubules (50% citric acid solution, 10 minutes, room temperature), then treated with a small drop of a 10% suspension (30 mg into 0.3 ml distilled water). Observations were then obtained using scanning electron microscopy.

Figure 4:
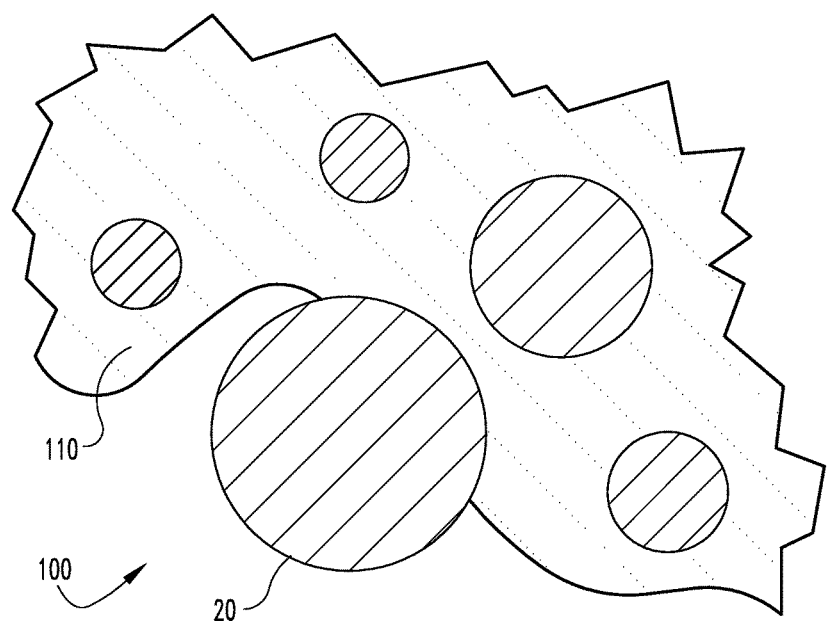
FIG. 4 illustrates a plan view of a microbead composition according to a second embodiment of the present novel technology.
Figure 5A:
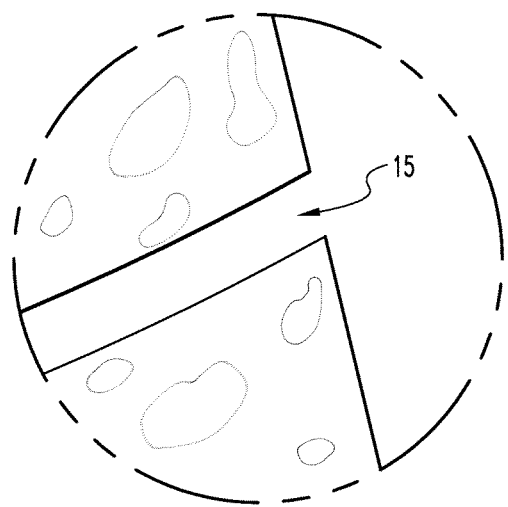
FIG. 5A is an enlarged view of dental tubules.
Figure 5B:
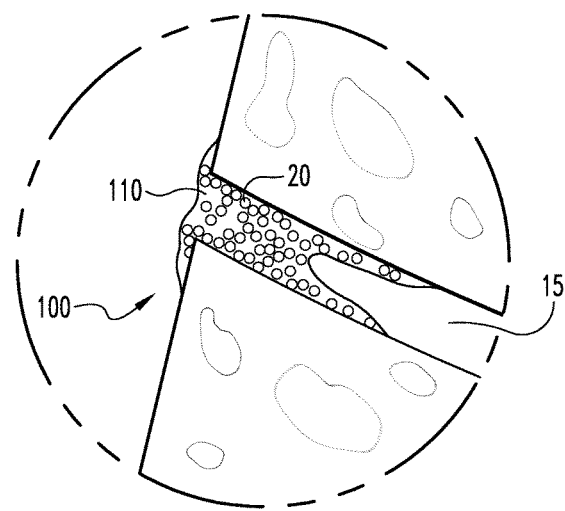
FIG. 5B is a schematic view of the tubule of FIG. 3A occluded with the composition of FIG. 4.
Figure 5C:
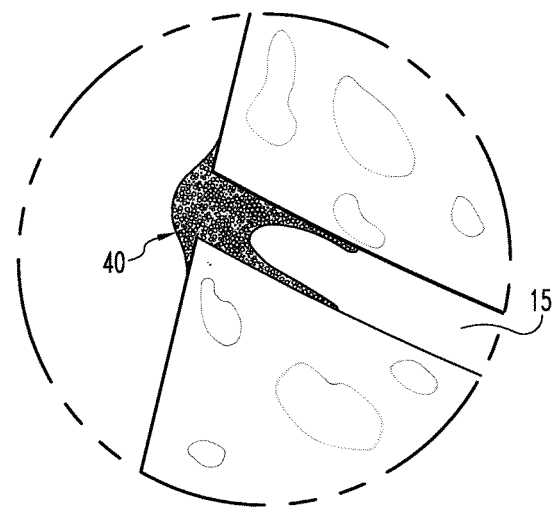
FIG. 5C is a schematic view of the tubule of FIG. 3A occluded with the composition of FIG. 4 after hardening into an agglomeration.

As illustrated in FIGS. 4 and 5A-5C, another embodiment of the present novel technology relates to a system 100 including a plurality of unfunctionalized or 'naked' microbeads 20, again typically having dimensions between 0.01 μm to 10 μm, and more typically between 0.9 μm and 3 μm, for packing within dentin tubules. More typically, microbeads 20 are provided with a particle size distribution (PED) defining a variety of diameters within this range for optimal packing and thus the provision of hypersensitivity benefits. Again, the microspheres 20 are typically composed of inorganic materials, such as silica, titania, glass (including bioresorbable glass such as 45S5 glass and like compositions), and/or organic materials such as polyethylene, polypropylene, cross-linked polymers and the like, or combinations thereof.

The microspheres 20 when introduced alone may penetrate readily into the dentin tubule 15, where they can agglomerate to form occlusions. Typically, the microspheres 20 are introduced with a dental delivery mechanism 110, such as a varnish, that both transports the microspheres 20 into the oral cavity to the dentition, and assists in adhering the microspheres 20 to the tubules 15. Once in the tubule 15, a plurality of microbeads 10 adhere to the tubule walls and to each other via the delivery fluid matrix 110 to define an agglomerate 40 that effectively occludes the tubule 15.

As with the functionalized microbead embodiment discussed above, this system 100 defined by unfunctionalized microbeads 20 suspended in a delivery fluid 110 defines a two-phase combination 100, comprising microspheres 20 suspended in a typically adhesive medium 110 for providing additional benefits relative to use of either agent alone. The unfunctionalized microsphere 20 may become adhered to a dentin surface via the delivery medium 110, such as varnish, despite challenge from an acid attack, providing structural stability and improved chemical resistance to demineralization from enamel and dentin. The varnish 110 likewise serves additional purposes, such as providing a sacrificial layer to subsequent acid attacks as well as to promote occlusion and/or remineralization through contact with saliva and various dental products with or without fluoride. These factors bear directly on the relief from dentin demineralization and therefore dental hypersensitivity. While either the microbeads 10 alone or the (typically organic) coating material 110 alone could offer hypersensitivity relief, the composite agglomerate 40 extends hypersensitivity relief.

EXAMPLE

Non-Functionalized Silica Microspheres.

The second example is a variant of the first example, wherein increasing occlusion is achieved using non-functionalized silica microspheres 20. The silica microspheres 20 are less than 3 μm in diameter and provide structural rigidity and resistance to acid attack of dentin. Much like the functionalized microspheres, the non-functionalized silica microspheres 20 are compatible with dentin and are able to attach to the walls of the tubules 15 as well as each other via the carrier medium 110, to participate in occluding dentin and obstructing future acidic interactions or erosion. These naked microspheres 20 may be implemented into dental vehicles 110 including varnishes, dentifrices, mouthwash and the like and may include fluoride agents to assist in whitening and dentin remineralization. The non-functionalized silica microspheres 20 have been observed to form agglomerates 40 that occlude the dentin tubules 15 and resist acid attack. Dentin specimens were demineralized for 10 minutes using 50% citric acid (pH=1.59). The specimens were then treated with the non-functionalized silica microspheres 20 in a 10% w/v suspension, and then again exposed to a subsequent 1% citric acid (pH=3.8) for 5 minutes. The study showed the microspheres' 20 ability to penetrate and remain in tubules 15 during the subsequent citric acid attack.

It will be appreciated that several of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

I claim:
1. A dental system, comprising:
   a dental matrix fluid; and
   a plurality of essentially spherical non-functionalized essentially silica microbeads suspended in the dental matrix fluid;
   wherein the respective essentially silica microbeads consist essentially of silica;
   wherein each respective essentially silica microbead is between about 0.1 micron and about 3 microns in diameter; and
   wherein all microbeads in the dental system are hydrophilic and essentially spherical.
2. The dental system of claim 1 wherein the dental matrix fluid includes fluoride.
3. A method for decreasing dental hypersensitivity, comprising:

a) selecting a plurality of non-functionalized essentially silica microbeads;
b) introducing the plurality of non-functionalized essentially silica microbeads into a delivery vehicle;
c) introducing the delivery vehicle into the oral cavity;
d) positioning respective non-functionalized microbeads into dental tubules; and
e) occluding dental tubules with non-functionalized microbeads; wherein the microbeads are essentially spherical;
wherein each respective microbead is between 0.1 μm to 3 μm diameter;
wherein all microbeads in the delivery vehicle are smooth, hydrophilic, and essentially spherical.

4. The method of claim 3, wherein the delivery vehicle is selected from the group comprising varnishes, dentifrices, mouthwashes, and combinations thereof.

5. A method for decreasing dental hypersensitivity, comprising:
a) sizing a plurality of non-functionalized essentially spherical silica microbeads to be between 0.1 μm to 3 μm in diameter, wherein the silica microbeads consist essentially of silica;
b) suspending the plurality of non-functionalized microbeads in a fluid matrix to define a dental delivery composition;
c) introducing the dental delivery composition into an oral cavity;
d) introducing respective non-functionalized microbeads into a dental tubule;
e) adhering respective functionalized microbeads to each other and to the dental tubule to define an aggregate; and
f) occluding the dental tubule with the aggregate;
wherein the surfaces of the microbeads are hydrophilic; and
wherein all microbeads in the dental delivery composition are essentially spherical.

6. The method of claim 5 wherein respective microbeads are added to a member of the group of dental vehicles including varnishes, dentifrices, mouthwash, and combinations thereof.

7. A dental hypersensitivity and whitening system, consisting essentially of:
at least two essentially spherical, inorganic essentially silica non-functionalized microbeads; and
a delivery medium;
wherein the at least two essentially spherical, inorganic essentially silica non-functionalized microbeads is suspended in the delivery medium to define a dental delivery composition; and
wherein each respective at least two generally spherical, inorganic non-functionalized microbeads is between 0.1 μm to 3 μm in diameter;
wherein all microbeads suspended in the delivery medium are essentially spherical and hydrophyllic.

8. The dental hypersensitivity and whitening system of claim 7, wherein the delivery medium is selected from the group comprising varnishes, dentifrices, mouthwashes, and combinations thereof.

9. The dental hypersensitivity and whitening system of claim 7, wherein the dental delivery system includes fluoride.

10. The dental hypersensitivity and whitening system of claim 7, wherein the delivery medium adheres to at least two essentially spherical, inorganic essentially non-functionalized microbeads and to dentin surfaces to define a composite aggregate, and wherein the composite aggregate provides dental remineralization and a sacrificial layer for acid resistance.

* * * * *